United States Patent
Zhu et al.

(10) Patent No.: US 7,725,171 B1
(45) Date of Patent: May 25, 2010

(54) SYSTEM AND METHOD FOR TRACKING ST SHIFT DATA UTILIZING HISTOGRAMS

(75) Inventors: Bing Zhu, Sunnyvale, CA (US); Jay Snell, Studio City, CA (US); Laleh Jalali, Moorpark, CA (US); Katie Hoberman, S. Pasadena, CA (US); Elizabeth Bacon, Portland, OR (US)

(73) Assignee: Pacesetter, Inc., Sunnyvale, CA (US)

( * ) Notice: Subject to any disclaimer, the term of this patent is extended or adjusted under 35 U.S.C. 154(b) by 294 days.

(21) Appl. No.: 11/848,606

(22) Filed: Aug. 31, 2007

(51) Int. Cl.
*A61B 5/04* (2006.01)

(52) U.S. Cl. .................................... 600/509
(58) Field of Classification Search .................. 600/509
See application file for complete search history.

(56) References Cited

U.S. PATENT DOCUMENTS

| | | | |
|---|---|---|---|
| 5,251,621 A | 10/1993 | Collins | |
| 5,388,578 A | 2/1995 | Yomtov | |
| 5,497,780 A | 3/1996 | Zehender | |
| 6,016,443 A | 1/2000 | Ekwall | |
| 6,021,350 A | 2/2000 | Mathson | |
| 6,108,577 A | 8/2000 | Benser | |
| 6,115,628 A | 9/2000 | Stadler et al. | |
| 6,128,526 A | 10/2000 | Stadler | |
| 6,162,183 A * | 12/2000 | Hoover | 600/534 |
| 6,256,538 B1 | 7/2001 | Ekwall | |
| 6,324,421 B1 | 11/2001 | Stadler et al. | |
| 6,368,284 B1 | 4/2002 | Bardy | |
| 6,468,263 B1 | 10/2002 | Fischell | |
| 6,937,899 B2 | 8/2005 | Sheldon et al. | |
| 2005/0059897 A1 | 3/2005 | Snell | |
| 2005/0113705 A1* | 5/2005 | Fischell et al. | 600/515 |
| 2006/0009811 A1 | 1/2006 | Sheldon | |
| 2006/0116593 A1 | 6/2006 | Zhang et al. | |
| 2006/0265020 A1 | 11/2006 | Fischell | |
| 2007/0093720 A1* | 4/2007 | Fischell et al. | 600/509 |
| 2007/0260285 A1* | 11/2007 | Libbus et al. | 607/9 |
| 2009/0048528 A1* | 2/2009 | Hopenfeld et al. | 600/516 |

FOREIGN PATENT DOCUMENTS

| | | |
|---|---|---|
| EP | 1164933 B1 | 5/2006 |
| WO | 0057781 A1 | 10/2000 |
| WO | 03020366 A1 | 3/2003 |
| WO | 03020367 A1 | 3/2003 |
| WO | 2004047917 A1 | 6/2004 |

\* cited by examiner

*Primary Examiner*—Carl H Layno
*Assistant Examiner*—Jeremiah T Kimball
(74) *Attorney, Agent, or Firm*—Steven M. Mitchell

(57) ABSTRACT

A method and system are provided for tracking ST shift data. The system includes an implantable medical device having an input configured to receive cardiac signals. Each cardiac signal has an associated heart rate and includes a segment of interest. The implantable medical device further includes a processor configured to determine segment variations of the segment of interest in the cardiac signals. The processor determines a heart rate associated with each of the segment variations with each heart rate falling within a corresponding heart rate range. The implantable medical device also includes a memory configured to store a group of histograms for a corresponding group of heart rate ranges. The histograms store distributions for the segment variations within corresponding heart rate ranges.

20 Claims, 13 Drawing Sheets

SYSTEM AND METHOD FOR TRACKING ST SHIFT DATA UTILIZING HISTOGRAMS

BACKGROUND OF THE INVENTION

Embodiments of the present invention pertain generally to implantable medical devices, and more particularly to implantable medical devices that track ST segment shifts utilizing histograms.

An implantable medical device is implanted in a patient to monitor, among other things, electrical activity of a heart and to deliver appropriate electrical and/or drug therapy, as required. Implantable medical devices ("IMDs") include, for example, pacemakers, cardioverters, defibrillators, implantable cardioverter defibrillators ("ICD"), and the like. The electrical therapy produced by an IMD may include, for example, pacing pulses, cardioverting pulses, and/or defibrillator pulses to reverse arrhythmias (e.g., tachycardias and bradycardias) or to stimulate the contraction of cardiac tissue (e.g., cardiac pacing) to return the heart to a normal sinus rhythm.

Cardiac ischemia is a condition whereby heart tissue does not receive adequate amounts of oxygen and is usually caused by a blockage of an artery leading to heart tissue. Ischemia arises during angina, acute myocardial infarction, coronary angioplasty, and any other condition that compromises blood flow to a region of tissue. When blockage of an artery is sufficiently severe, the cardiac ischemia becomes an acute myocardial infarction (AMI) also referred to as a myocardial infarction (MI) or a heart attack.

Many patients at risk of cardiac ischemia have pacemakers, ICDs or other medical devices implanted therein. Electrocardiograms (ECG) acquired from these devices are useful for diagnosing ischemia and locating damaged areas within the heart. ECGs are composed of various waves and segments that represent the heart depolarizing and repolarizing. An ST segment (STS) represents the portion of the cardiac signal between ventricular depolarization and ventricular repolarization.

Techniques have been developed for detecting cardiac ischemia using implanted medical devices. Some conventional IEGM-based ischemia detection techniques seek to detect ischemia by identifying changes in the elevation of the STS from the baseline of the IEGM that occur during cardiac ischemia. Elevation of the STS in an IEGM (e.g., an acute voltage shift in the STS of an IEGM) may result when there are abnormalities in the polarizations of cardiac tissue during an acute myocardial infraction (MI). Deviation of the STS from a baseline is a result of injury to cardiac muscle, changes in the synchronization of ventricular muscle depolarization, drug or electrolyte influences, or the like.

STS variations or deviations, for example, voltage shifts in the STS of an intracardiac electrogram in an ICD or pacemaker can be recorded and stored in different formats for analysis. For example, STS variations can be stored as STS histograms that may be used to assess and evaluate the existence, exacerbation and alleviation of myocardial ischemia. The STS variation histograms may include a plurality of different bins representing events or values corresponding to the STS variation data. The bins store data that can be used to track the occurrence of the events or data. For example, event or data counts may be stored in each of the bins corresponding to a particular event or data value (or range of data values). The bins may correspond, for example, to incrementally changing variances of the mean of the STSs.

However, conventional implantable devices do not allow tracking of a patient's STS variations for heart rate ranges over different periods of times, for example, using STS histograms. These conventional implantable devices typically store raw STS and other cardiac data. The amount of collected raw data increases rapidly. However, the storage capacity of these implantable medical devices may be limited and not allow much raw data to be collected over a certain time period. For example, the memory within these implantable devices may not be able to store the total amount of collected raw data over a period of time (e.g., a period of interest), thereby resulting in some of the data being deleted. Accordingly, conventional devices may not provide sufficient information over a sufficient time period of time to allow for proper analysis of STS information to determine ischemic conditions and the like. Thus, a need remains for tracking in implantable medical devices STS variations for heart rate ranges over different periods of time using STS histograms.

SUMMARY

In accordance with at least one embodiment, an implantable medical device is provided that includes an input configured to receive cardiac signals. Each cardiac signal has an associated heart rate and includes a segment of interest. The implantable medical device further includes a processor configured to determine segment variations of the segment of interest in the cardiac signals. The processor determines a heart rate associated with each of the segment variations with each heart rate falling within a corresponding heart rate range. The implantable medical device also includes a memory configured to store a group of histograms for a corresponding group of heart rate ranges. The histograms store distributions for the segment variations within corresponding heart rate ranges.

In accordance with another embodiment, a method is provided for maintaining myocardial data in an implantable medical device. The method includes receiving myocardial data including segments of interest and associating the segments of interest with heart rate ranges. The method further includes generating a group of histograms corresponding to each of the heart rate ranges. The group of histograms include distributions for segment variations for the segments of interest. The method also includes storing the group of histograms in the implantable medical device.

In accordance with yet another embodiment, a computer readable medium for use in an implantable medical device having a memory and a programmable controller is provided. The computer readable medium includes instructions to direct the programmable controller to receive myocardial data including segments of interest and associate the segments of interest with heart rate ranges. The instructions further direct the programmable controller to generate a group of histograms corresponding to each of the heart rate ranges. The group of histograms include distributions for segment variations for the segments of interest. The instructions also direct the memory to store the group of histograms in the implantable medical device.

DETAILED DESCRIPTION

In the following detailed description, reference is made to the accompanying drawings that form a part hereof, and in which is shown by way of illustration specific embodiments in which various embodiments of the present invention may be practiced. It is to be understood that the embodiments may be combined, or that other embodiments may be utilized and that structural, logical and electrical changes may be made without departing from the scope of the various embodiments of the present invention. For example, embodiments may be used with a pacemaker, a cardioverter, a defibrillator, and the like. The following detailed description is, therefore, not to be taken in a limiting sense, and the scope of the various embodiments of the present invention is defined by the appended claims and their equivalents. In this document, the terms "a" or "an" are used, as is common in patent documents, to include one or more than one. In this document, the term "or" is used to refer to a nonexclusive or, unless otherwise indicated.

Figure 1:
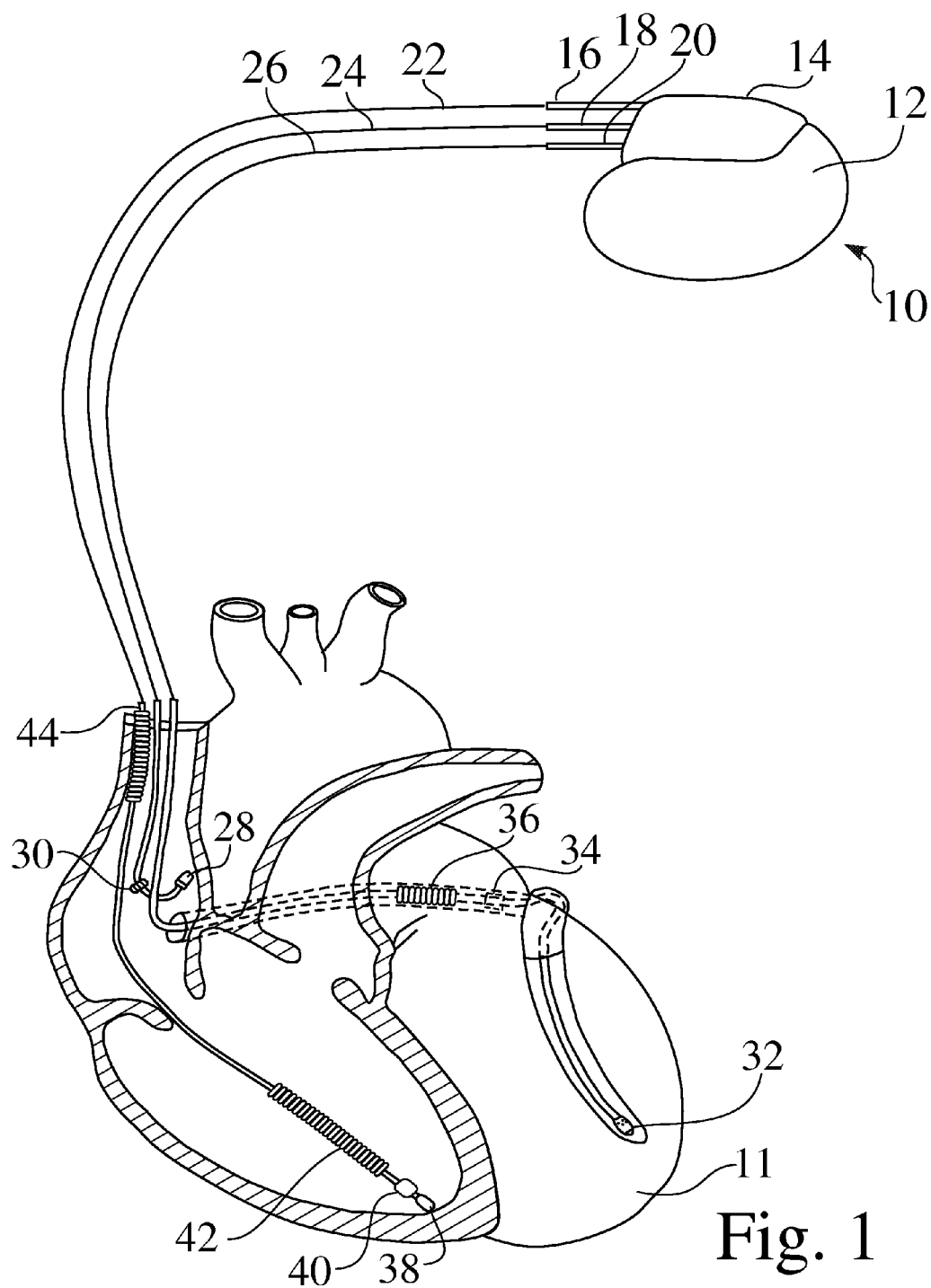
FIG. 1 illustrates an implantable medical device formed in accordance with an embodiment of the present invention.

FIG. 1 illustrates an implantable medical device 10 (IMD) that is coupled to a heart 11. The implantable medical device 10 may be a cardiac pacemaker, an implantable cardioverter defibrillator (ICD), a defibrillator, implantable cardioverter/defibrillators (ISCDs), or an ICD coupled with a pacemaker implemented in accordance with an embodiment of the present invention. The IMD 10 may be a dual-chamber stimulation device capable of treating both fast and slow arrhythmias with stimulation therapy, including cardioversion, defibrillation, and pacing stimulation, as well as capable of detecting heart failure, evaluating its severity, tracking the progression thereof, and controlling the delivery of therapy and warnings in response thereto. As explained below in more detail, the IMD 10 may be controlled to monitor cardiac signals and to identify potentially abnormal physiology (e.g., ischemia).

The IMD 10 includes a housing 12 that is joined to a header assembly 14 (e.g., an IS-4 connector assembly) that holds receptacle connectors 16, 18, and 20 that are connected to a right ventricular lead 22, a right atrial lead 24, and a coronary sinus lead 26, respectively. The leads 22, 24 and 26 may be located at various locations, such as an atrium, a ventricle, or both to measure the physiological condition of the heart 11. One or more of the leads 22, 24 and 26 detect cardiac signals that form an electrical activity indicator of myocardial function over multiple cardiac cycles. To sense atrial cardiac signals and to provide right atrial chamber stimulation therapy, the right atrial lead 24 includes at least an atrial tip electrode 28, which is typically implanted in the right atrial appendage, and an atrial ring electrode 30. The cardiac signals represent analog signals that are subsequently digitized and analyzed to identify waveforms of interest. Examples of waveforms identified from the cardiac signals include the P-wave, T-wave, the R-wave, the QRS complex and the like that are used to describe, for example, electrocardiograms (ECGs) and intracardiac electrograms (IEGMs). The waveforms of interest may be collected over a period of time and the information associated therewith provided in different formats, for example, in ST histograms. While P-waves, R-waves and T-waves may be generally considered features of a surface electrocardiogram (ECG), for convenience and generality, herein the terms R-wave, T-wave and P-wave are also used to refer to the corresponding internal cardiac signal, such as an intracardiac electrogram (IEGM).

The coronary sinus lead 26 receives atrial and ventricular cardiac signals and delivers left ventricular pacing therapy using at least a left ventricular tip electrode 32, left atrial pacing therapy using at least a left atrial ring electrode 34. Optionally, a left atrial coil electrode 36 may be used for one or both of pacing and/or shock therapy. The right ventricular lead 22 has a right ventricular tip electrode 38, a right ventricular ring electrode 40, a right ventricular (RV) coil electrode 42, and a SVC coil electrode 44. Therefore, the right ventricular lead 22 is capable of receiving cardiac signals and delivering stimulation in the form of pacing and shock therapy to the right ventricle.

Figure 2A:
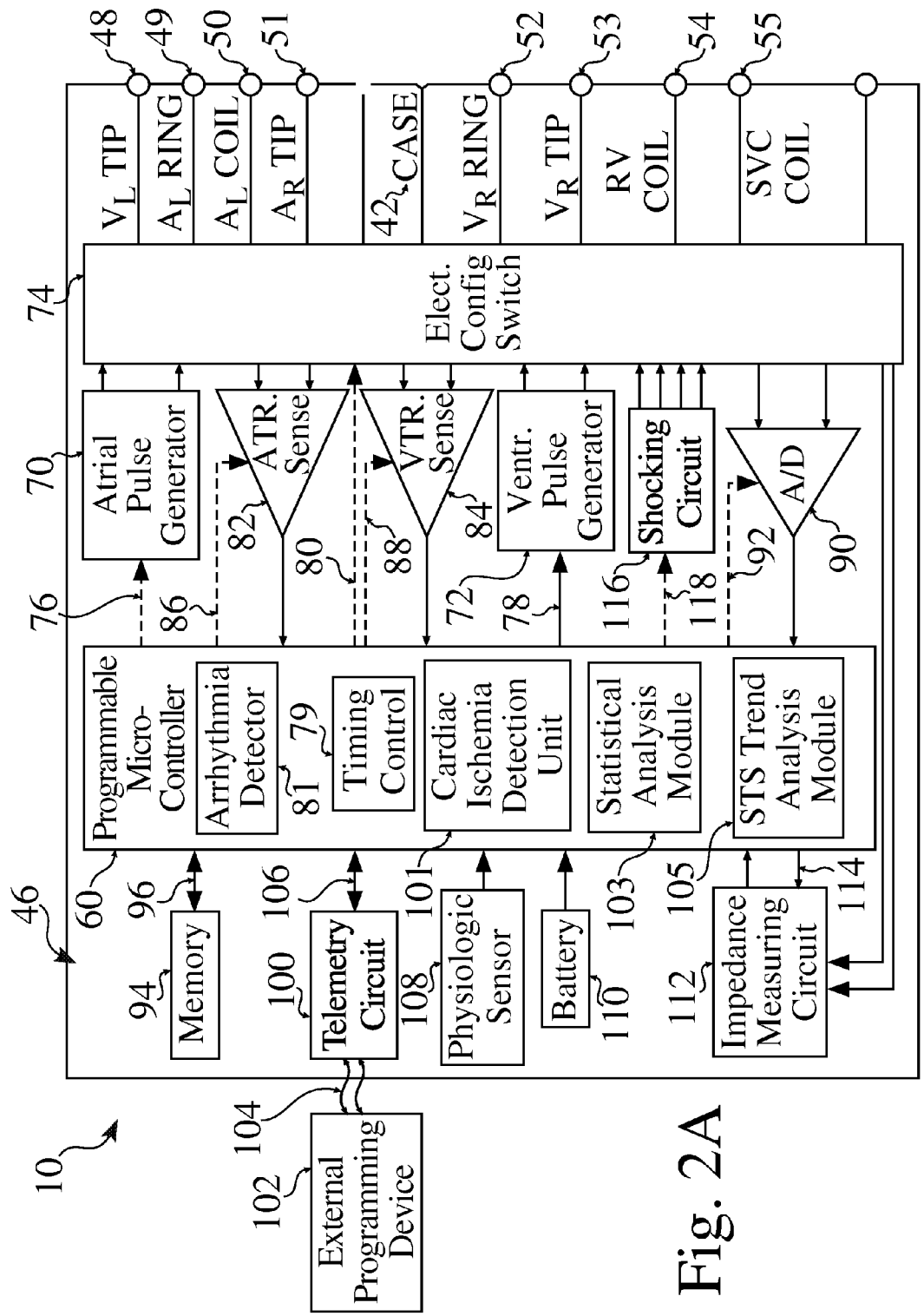
FIGS. 2A and 2B illustrate a functional block diagram of exemplary internal components of an implantable medical device formed in accordance with an embodiment of the present invention.
Figure 2B:
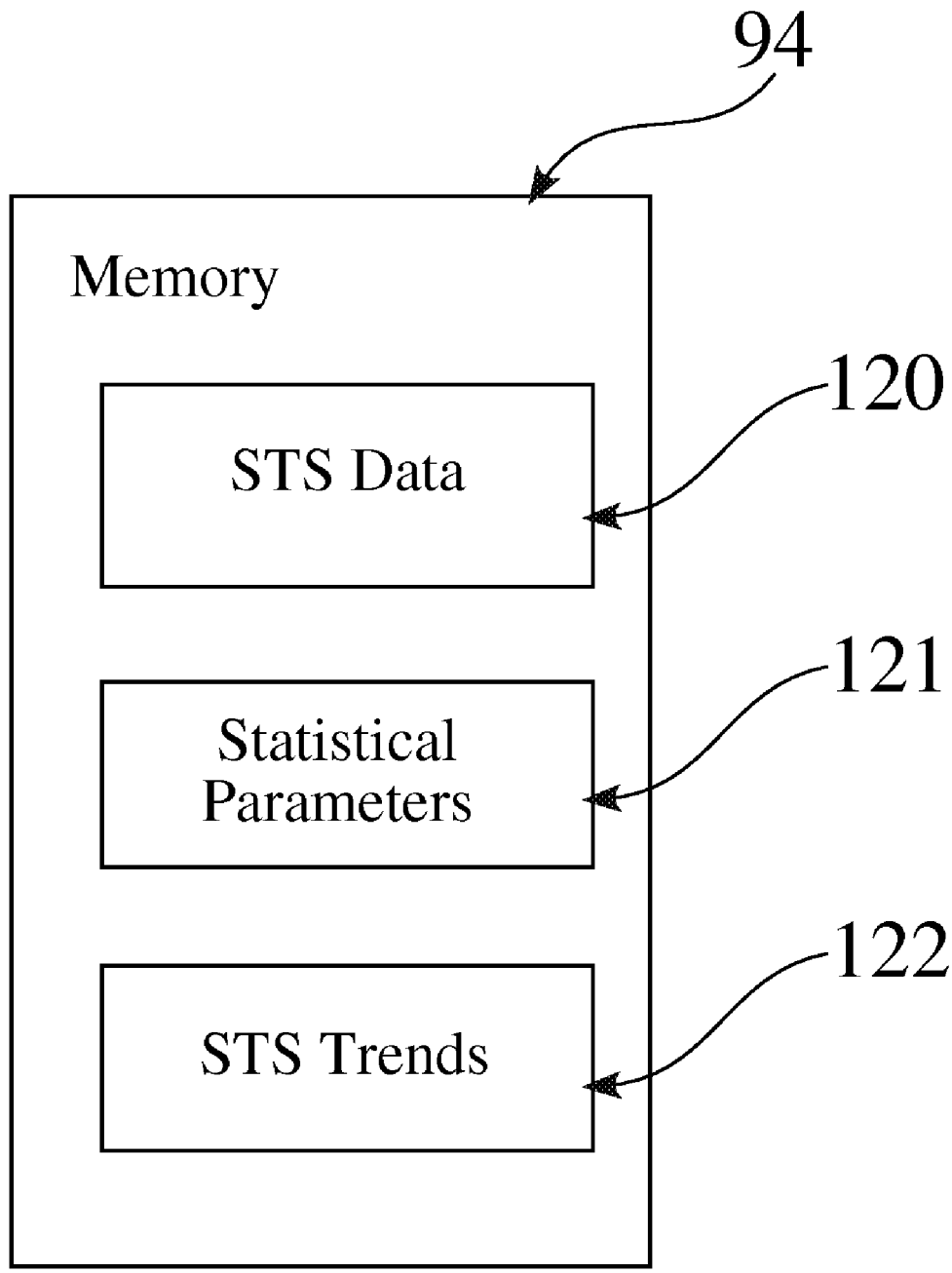

FIGS. 2A and 2B illustrate a block diagram of exemplary internal components of the IMD 10. The IMD 10 is for illustration purposes only, and it is understood that the circuitry could be duplicated, eliminated or disabled in any desired combination to provide a device capable of treating the appropriate chamber(s) of the heart with cardioversion, defibrillation, and/or pacing stimulation.

The housing 46 for IMD 10 (shown schematically in FIG. 2A), is often referred to as the "can", "case" or "case electrode" and may be programmably selected to act as the return electrode for all "unipolar" modes. The housing 46 further includes a connector (not shown) having a plurality of terminals, namely a right atrial tip terminal ($A_R$ TIP) 51, a left ventricular tip terminal ($V_L$ TIP) 48, a left atrial ring terminal ($A_L$ RING) 49, a left atrial coil terminal ($A_L$ COIL) 50, a right ventricular tip terminal ($V_R$ TIP) 53, a right ventricular ring terminal ($V_R$ RING) 52, a right ventricular shocking terminal (RV COIL) 54, and an SVC shocking terminal (SVC COIL) 55.

The IMD 10 includes a programmable microcontroller 60, which controls the operation of the IMD 10 based on acquired cardiac signals. The IMD 10 may collect the cardiac signals (e.g., ST segment (STS) variations) and transmit the cardiac signals to a remote device without any subsequent analysis of the cardiac data and/or store the cardiac signals. Optionally, IMD 10 may collect the cardiac signals and process the cardiac signals (e.g., determine a statistical parameter and STS trends), and transmit the cardiac signals and the statistical parameters and STS trends. Alternatively, IMD 10 may calculate the statistical parameters, but not calculate any STS trends, and transmit the statistical parameters to a remote site. In one example, the microcontroller 60 monitors the cardiac signals to identify therein STS variations and determine a potential ischemic condition. A cardiac ischemia detection unit 101 controls the detection of episodes of cardiac ischemia. The microcontroller 60 (also referred to herein as a processor module or unit) typically includes a microprocessor, or equivalent control circuitry, may be configured to control the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in memory. Among other things, the microcontroller 60 receives, processes, and manages storage of digitized data from the various electrodes.

The microcontroller 60 may also analyze the data, for example, in connection with collecting, over a period of time, reference STS variations in a cardiac signal (e.g., sense signals received from leads 22, 24 and 26). The microcontroller 60 may also measure STS variations and compare the variations to the STS threshold to identify a potential abnormal physiology (e.g., such as when the patient is having a post-myocardial infarct, a "silent" myocardial infarct, a myocardial infarct, an ischemia, a heart block, an arrhythmia, fibrillation, congestive heart failure, and the like). A statistical analysis module 103 examines the raw STS variation data collected over multiple data collection periods to determine a linear regression line (e.g., simple linear regression, least squares regression line, and the like) that best fits the raw STS variation data. The statistical analysis module 103 may also use the raw STS variation data to create one or a collection of histograms. The histogram(s) may be used to determine statistical parameters (e.g., an average, an average deviation, a standard deviation, and the like). An STS trend analysis module 105 utilizes multiple histograms and various statistical parameters to construct an STS trend that can be used to predict future ischemic events in a patient.

The IMD 10 includes an atrial pulse generator 70 and a ventricular pulse generator 72 to generate pacing stimulation pulses. Microcontroller 60 includes timing control circuitry 79 that is used to control the timing of such stimulation pulses. In order to provide stimulation therapy in a desired number of chambers of the heart, the atrial and ventricular pulse generators, 70 and 72, may include dedicated, independent pulse generators, multiplexed pulse generators or shared pulse generators. The pulse generators, 70 and 72, are controlled by the microcontroller 60 via appropriate control signals, 76 and 78, respectively, to trigger or inhibit the stimulation pulses.

Switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, etc.) by selectively closing the appropriate combination of switches (not shown) as is known in the art. For arrhythmia detection, arrhythmia detector 81 utilizes atrial sensing circuits 82 and ventricular sensing circuits 84 to sense whether a cardiac rhythm is physiologic or pathologic. The atrial sensing circuits 82 and ventricular sensing circuits 84 may also be selectively coupled to the leads through the switch 74 for detecting the presence of cardiac activity in each of the four chambers of the heart. Control signals 86 and 88 from processor 60 direct output of the atrial and ventricular sensing circuits, 82 and 84, that are connected to the microcontroller 60. In this manner, the atrial and ventricular sensing circuits, 82 and 84 are able to trigger or inhibit the atrial and ventricular pulse generators, 70 and 72.

The cardiac signals are applied to the inputs of an analog-to-digital (A/D) data acquisition system 90. The data acquisition system 90 is configured to acquire cardiac signals, convert the raw analog data into a digital cardiac signal, and store the digital cardiac signals in memory 94 for later processing and/or telemetric transmission to an external device 102. Control signal 92 from processor 60 determines when the data acquisition system 90 acquires signals, stores the signals in memory 94, or transmits data to an external device 102. The data acquisition system 90 is coupled to the right atrial lead 24, the coronary sinus lead 26, and the right ventricular lead 22 through the switch 74 to sample cardiac signals across any combination of desired electrodes.

The microcontroller 60 is coupled to the memory 94 by a suitable data/address bus 96, wherein the programmable operating parameters used by the microcontroller 60 are stored and modified, as required, in order to customize the operation of IMD 10 to suit the needs of a particular patient. The memory 94 may also store data indicative of myocardial function, such as the cardiac data, STS variations, reference STS variations, and STS variation thresholds and the like for a desired period of time (e.g., one hour, 24 hours, or one month). The memory 94 may store instructions to direct the microcontroller 60 to analyze the data to detect ischemia and/or to identify events of interest. For example, the memory 94 (as shown in FIG. 2B) may store STS variation data 120, statistical parameters 121, and STS trends 122. The STS variation data 120 may be the raw STS variations for the patient collected during a data collection period that corresponds to a variation in the STS that exceeds a predetermined threshold.

The memory 94 stores a group of histograms for corresponding groups of heart rate ranges, where the histograms each store a distribution for ST variations within the corresponding heart rate range. For example, the ST variations may be segment variations with respect to a reference level, with the reference level presenting one of i) a baseline value for the segment of interest and ii) a value for a reference segment with the cardiac signal. The different groups of histograms may store distributions of segment variations over different time periods (e.g., short term and long term) and may maintain a running average of distributions for the segment variations. For example, the histograms may include a series of bins corresponding to different segment variations with the bins being automatically normalized when a count in at least one of the bins reaches a maximum count as described in more detail below.

Figure 8:
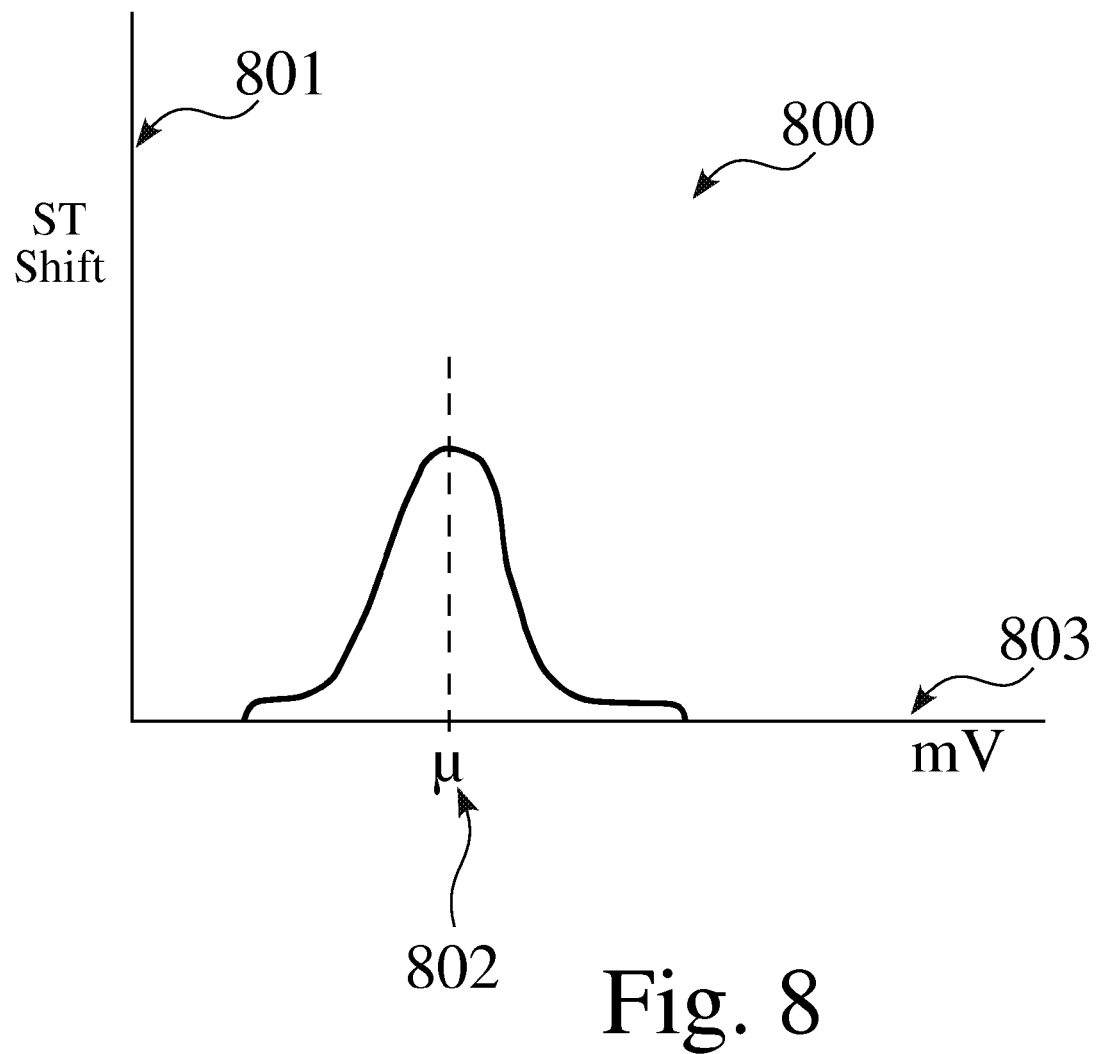
FIG. 8 illustrates a histogram of STS variations utilized in accordance with an embodiment of the present invention.
Figure 9:
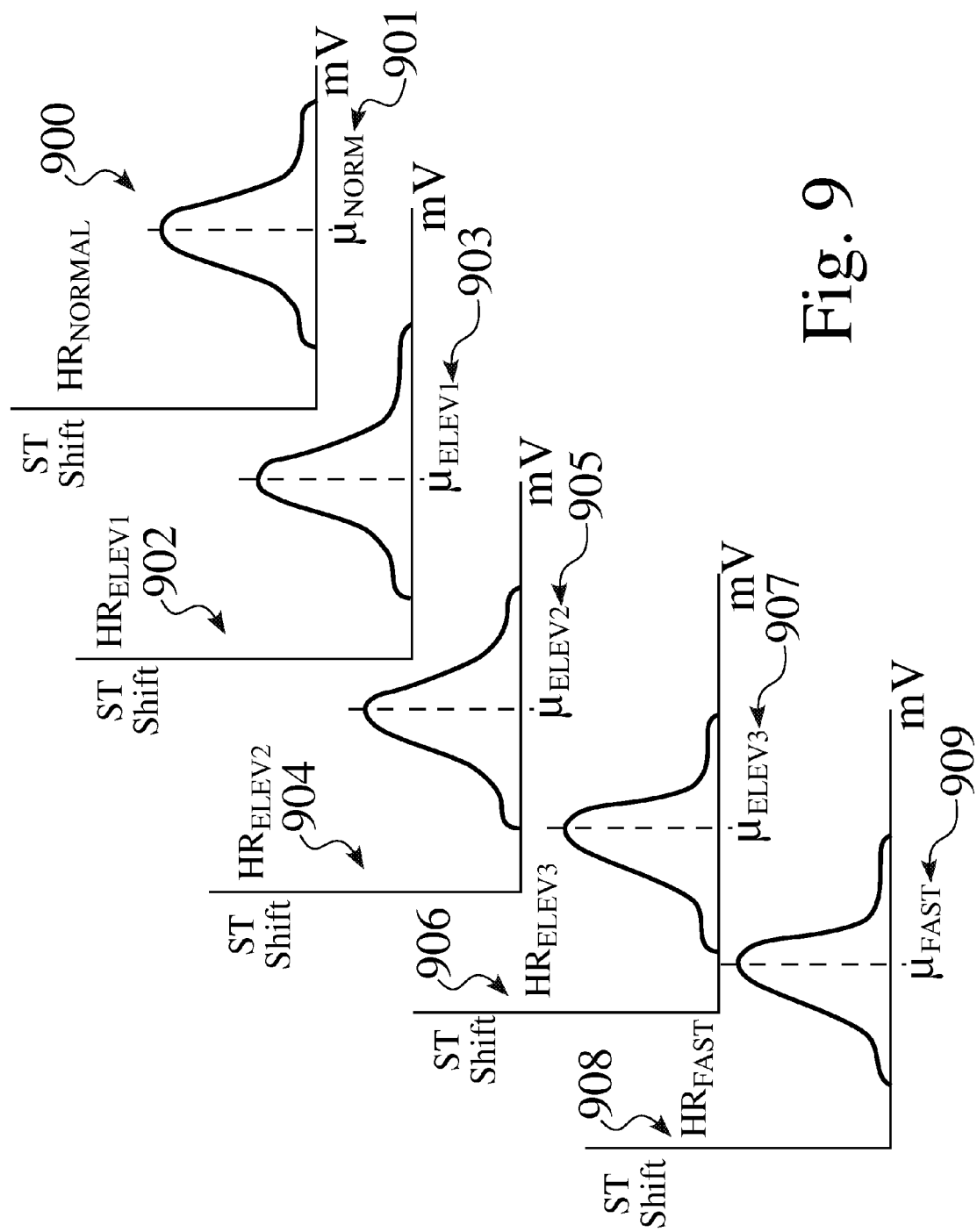
FIG. 9 illustrates a set of histograms for multiple data collection periods from which statistical parameters are derived in accordance with an embodiment of the present invention.

The statistical parameters 121 are created by the statistical analysis module 103 (shown in FIG. 1) that may be derived from a histogram 800 (shown in FIG. 8) and the statistical parameters may include an average, an average deviation, a standard deviation, and the like. The statistical parameters 121 may also correspond to multiple histograms (as shown in FIG. 9), which have the STS variations sorted according to bins (e.g., variance bins corresponding to less than 40 beats per minute (bpm), 40-60 bpm, 60-90 bpm, and greater than 90 bpm) for a particular data collection period. The STS trends 122 are created by the STS trend analysis module 105 (shown in FIG. 2A) and are described below.

The operating parameters of the IMD 10 may be non-invasively programmed into the memory 94 through a telemetry circuit 100 in communication with the external device 102, such as a programmer, trans-telephonic transceiver or a diagnostic system analyzer. The telemetry circuit 100 is activated by the microcontroller 60 by a control signal 106. The telemetry circuit 100 allows cardiac signals and status information relating to the operation of IMD 10 (as contained in the microcontroller 60 or memory 94) to be sent to the external device 102 through an established communication link 104.

The IMD 10 additionally includes a battery 110, which provides operating power to all of the circuits shown within the housing 46, including the processor 60. The IMD 10 is shown as having an impedance measuring circuit 112 that is enabled by the microcontroller 60 via a control signal 114. The impedance measuring circuit 112 is advantageously coupled to the switch 74 so that impedance at any desired electrode may be obtained. The IMD 10 also includes a physiologic sensor 108 that may be used to adjust pacing stimulation rate according to the exercise state of the patient.

In the case where IMD 10 is intended to operate as an implantable cardioverter/defibrillator (ISCD) device, the IMD 10 detects the occurrence of an STS variation that indicates an arrhythmia and automatically applies an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5-10 joules) or high energy (11 to 40 joules), as controlled by the microcontroller 60. Such shocking pulses are applied to the heart 11 of the patient through at least two shocking electrodes, and as shown in this embodiment, selected from the left atrial coil electrode 36, the RV coil electrode 42, and/or the SVC coil electrode 44.

Figure 3:
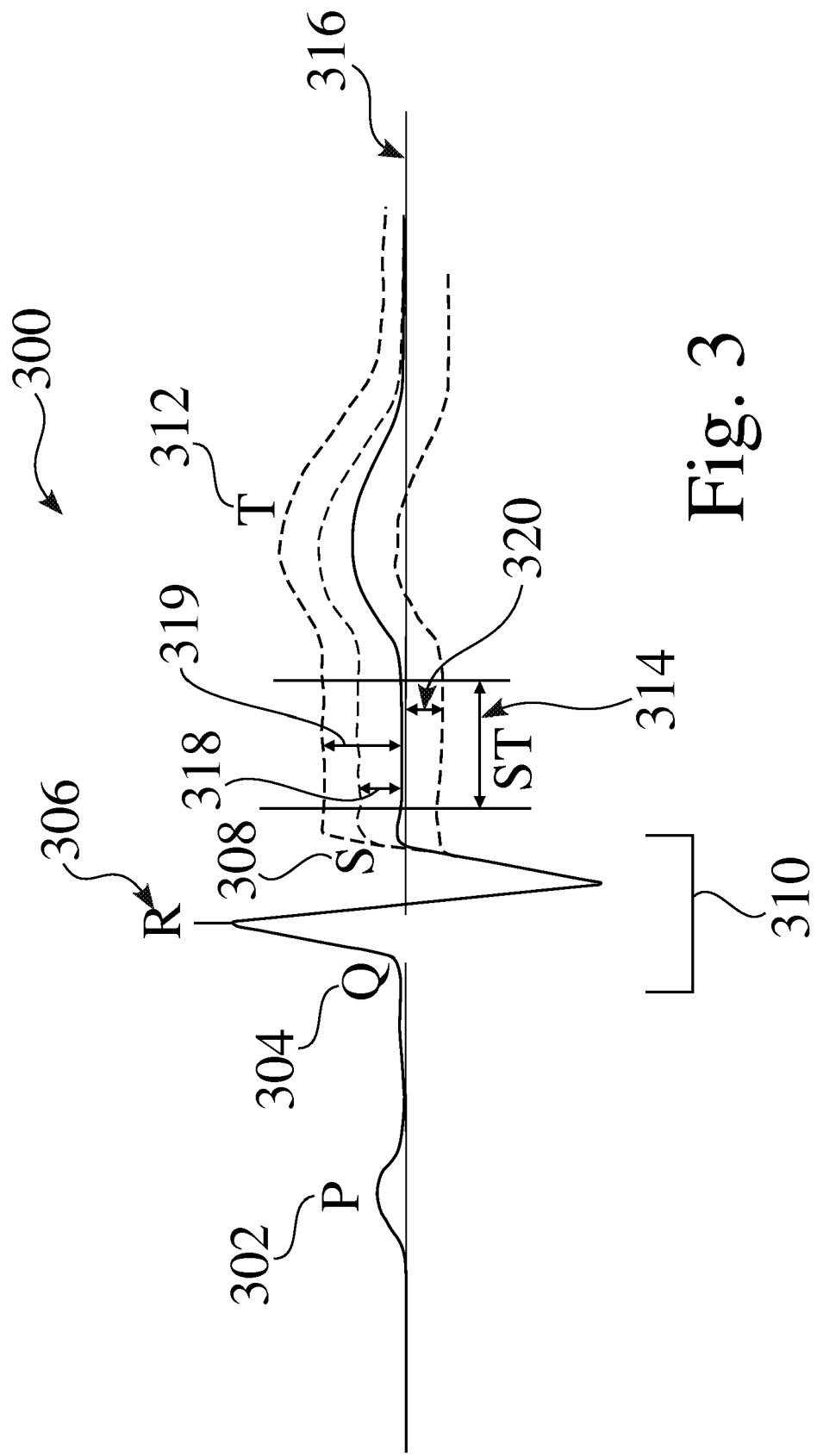
FIG. 3 illustrates an exemplary diagram of a typical electrocardiogram and potential STS variations utilized in accordance with an embodiment of the present invention.

FIG. 3 illustrates a single cardiac cycle 300 composed of a P-wave 302, a Q-wave 304, an R-wave 306, an S-wave 308 and a T-wave 312. The cardiac cycle 300 may represent cardiac signals, such as intra-cardiac electrogram (IEGM) signals, electrocardiogram (ECG) signals and the like. The horizontal axis represents time, while the vertical axis is defined in units of voltage. An abnormal cardiac signal indicates a potential ischemic condition. The Q-wave 304, R-wave 36 and S-wave 308 together define a QRS complex 310. The QRS complex 310 is used to locate the R-wave 306 to determine a baseline 316. The portion of the signal between the S-wave 308 and T-wave 312 constitutes an STS 314. As shown, the STS 314 may have a voltage level that aligns with the voltage level of the baseline 316. Alternatively, the STS 314 may have a voltage level that is shifted above 318, 319 or shifted below 320 the baseline 316. STS variations may occur above or below the baseline 316. Alternatively, STS variations may include ST deviations or STS. An ST deviation is determined by subtracting the level of a PQ segment 303 from the level of the STS 314 for one heartbeat. The ST deviation provides a measure of the change in variability over a period of time.

An STS is determined by changes in the ST deviation over a period of time. For example, a current STS may be calculated by subtracting a stored baseline ST deviation from a newly acquired ST deviation. ST deviations and STSs may be calculated as averages over multiple cardiac cycles as well. Deviations of the voltage level of the STS 314 may be a result of injury to cardiac muscle, changes in the synchronization of ventricular muscle depolarization, drug or electrolyte influences, and the like. The voltage elevation of the STS, as shown by 318 and 319, in a cardiac signal may result when there are abnormalities in the polarizations of cardiac tissue during an acute myocardial infraction (MI). The STS variations 318-320 may arise because of differences in the electrical potential between cells that have become ischemic and cells that are still receiving normal blood flow. Thus, the STS variations 318-320 are a reliable indicator of the possibility of ischemia. It is recognized that STS 314 may deviate due to non-ischemic events.

Figure 4:
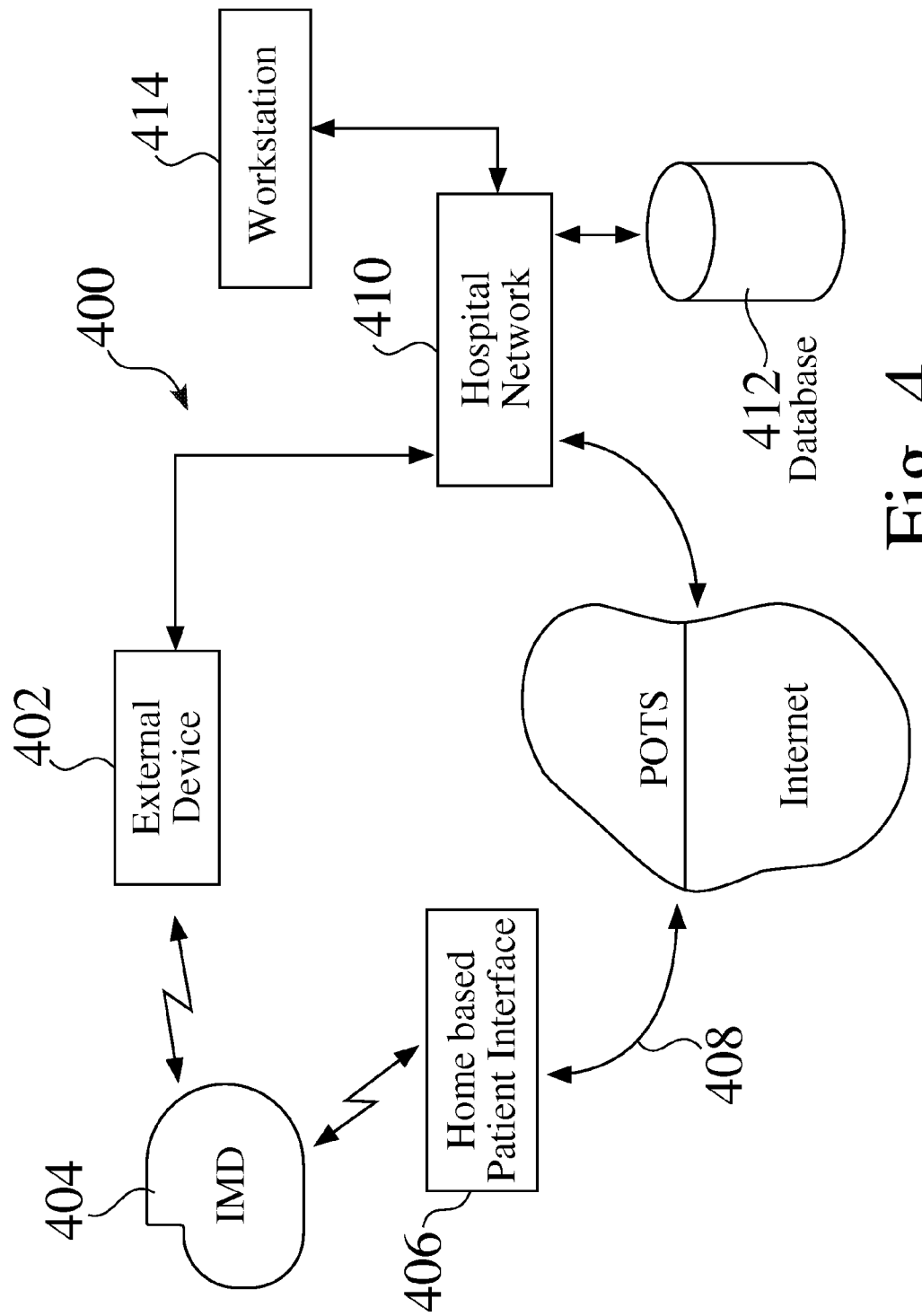
FIG. 4 illustrates a block diagram of an exemplary patient care system implemented in accordance with an embodiment of the present invention.

FIG. 4 illustrates a block diagram of an exemplary patient care system 400 implemented in accordance with an embodiment. The patient care system 400 may include an external device 402, such as a programmer, that is operated by a physician. The external device 402 wirelessly communicates with an IMD 404. The IMD 404 may also communicate wirelessly with a home-based patient interface device 406. The interface device 406 may include a personal computer, hand-held device, and the like, that has the ability to wirelessly communicate with the IMD 404. The interface device 406 is joined, over a communications link 408, through the Internet or a plain old telephone service (POTS), with a network, for example, a hospital network 410. The hospital network 410 is joined to one or more workstations 414 and to a database 412 that may store, among other things, patient records and the like. The hospital network 310 also communicates with the external device 402. The workstations 414 may represent personal computers, PDAs, laptop computers, cell phones and the like. The workstations 414 permit physicians to analyze, monitor, and diagnose myocardial function based on data collected by the IMD 404. The patient care system 400 is configured to implement one or more algorithms for detecting ischemia.

STS variations stored in the IMD 404, for example, as groups of STS variation distribution histograms, may be communicated to the hospital network 410 via the external device 402 or through the home based patient interface 406 via the communication link 408. Using this communication arrangement, the histograms are downloaded from the memory of the IMD 404 and then stored locally, for example, within the database 412 or other memory/data storage forming part of or connected to the hospital network 410 or the external device 402. The stored histograms then may be displayed on the workstations 414 or external device (or alternatively displayed directly from the downloaded data without storing locally). For example, the one or more histograms may be displayed separately or together on a display of the workstation 414 or the external device 402. A user (e.g., doctor) may access different histograms for display, for example, different histograms corresponding to different time periods, different heart ranges or a combination thereof. The displayed histogram(s) then may be reviewed or analyzed.

Figure 5:
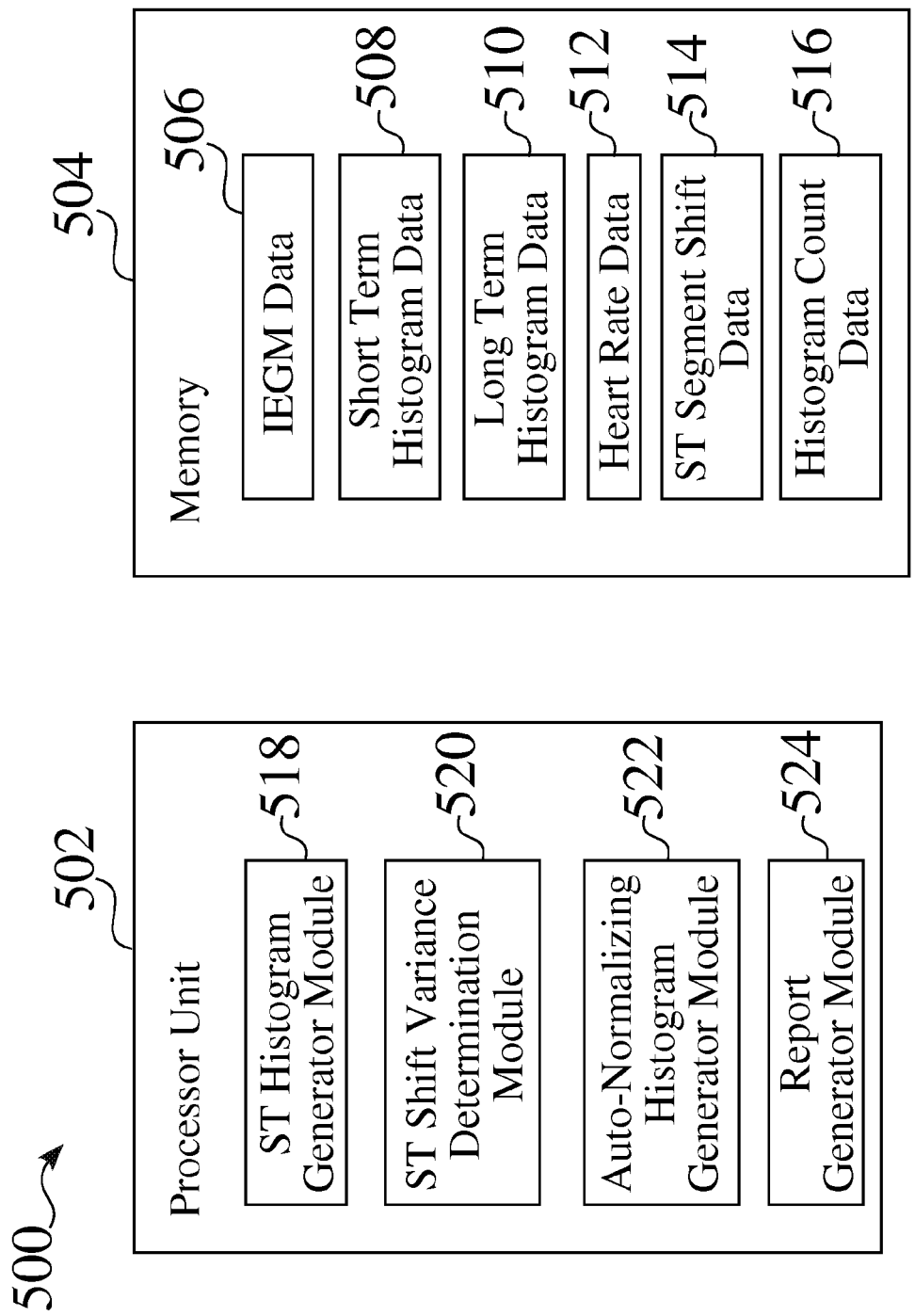
FIG. 5 illustrates a block diagram of an ischemia detection module that may be implemented in accordance with an embodiment of the invention.

FIG. 5 illustrates a block diagram of an ischemia detection module 500 that is configured to be implemented within any of the IMD 10, IMD 404, external device 402, interface device 406, workstations 414 and hospital network 410. The ischemia detection module 500 generally includes a processor unit 502 and a memory 504. When implemented within the IMD 10, the memory 504 may represent a portion of the memory 94 (shown in FIG. 2A), or alternatively a separate memory module within the IMD 10. The memory 504 is configured to store, as digital data streams, one or more of IEGM data 506, short term histogram data 508 (e.g., weekly histogram data or daily histogram data), long term histogram data 510 (e.g., monthly ST histogram data or yearly ST histogram data) and heart rate data 512. In general, long term histogram data 510 is any data corresponding to a time period longer than the time period corresponding to short term histogram data 508.

The memory 504 may store statistical parameters that are calculated, for one or more cardiac cycles, based upon the digital data streams for the select period. The statistical parameters may include, by way of example only, one or more of IEGM parameters, such as, STS variations, T-wave morphology, QT Max values, QT deviation values, PR values and the like. For example, STS data 514 may be stored. The STS data 514 may be stored over different heart rate ranges, which may be automatically normalized (auto-normalized) as described herein. For example, one histogram may be stored for each heart rate range. Histogram count data 516 also may be stored in the memory 504. The histogram count data 516 may correspond to bin counts associated with a value or event, or a range or values or events, which are incremented (e.g., a bin is incremented by one) upon the occurrence of an event or sampling of a value.

The processor unit 502 includes one or more dedicated processors and/or multipurpose processors that are programmed to acquire and process cardiac signals to determine segment variations for segments of interest, for example, STSs, of the acquired cardiac signals. The STSs may be determined for a heart rate falling within a corresponding heart rate range. In various embodiments, the processor unit 502 includes an ST histogram generator module 518 that generates different histograms as described herein. For example, the ST histogram generator module 518 acquires STS data from the IEGM data 506. The STS data may be stored on a heartbeat by heartbeat basis or on a set by set basis, which may be stored periodically. The values for the STSs may be stored in histogram bins and define histogram count data 516. The values may be stored based on a heart rate range as determined using the heart rate data 512.

Figure 6A:
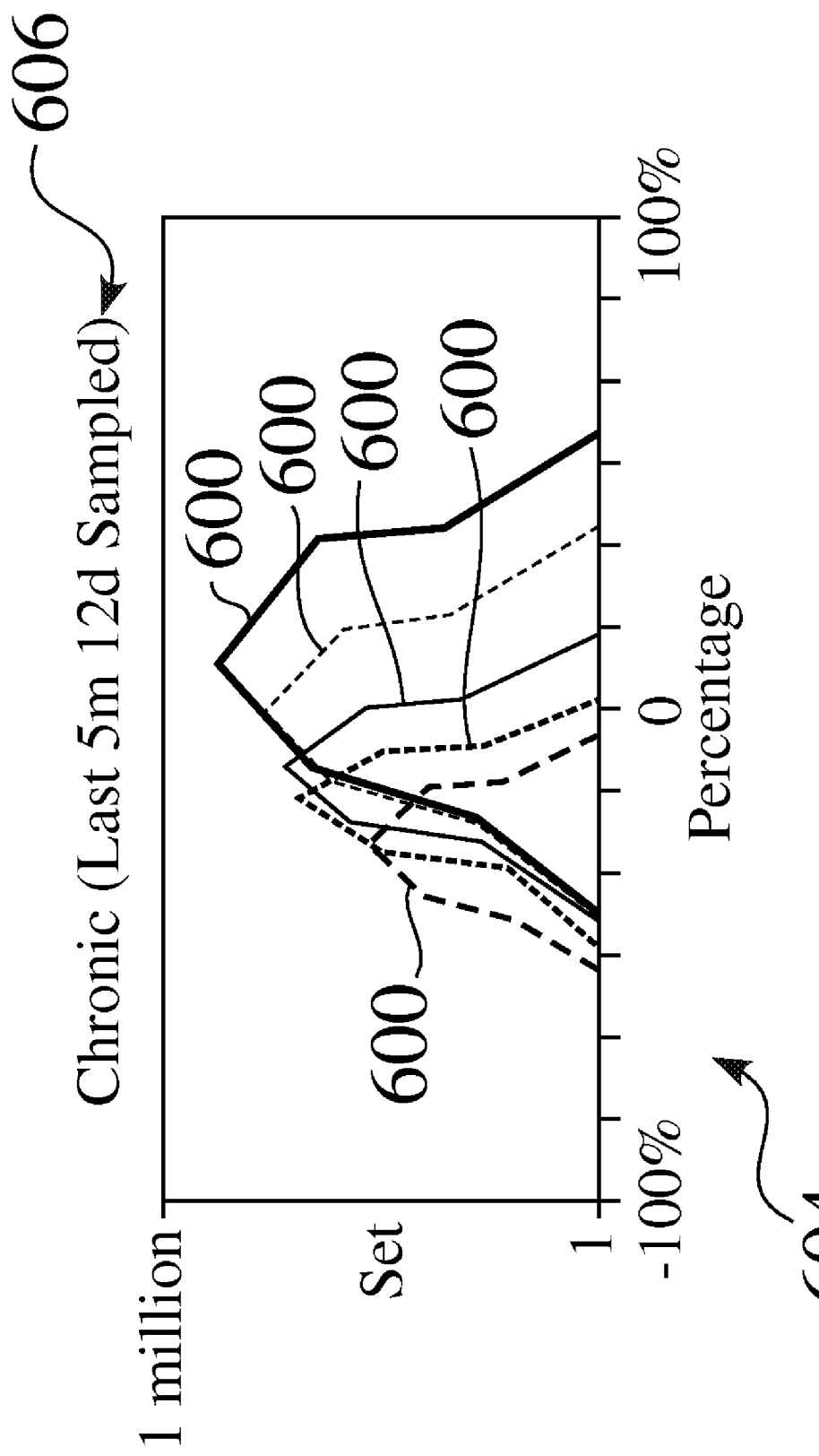
FIGS. 6A and 6B illustrate groups of histograms corresponding to different time periods derived in accordance with an embodiment of the present invention.
Figure 6B:
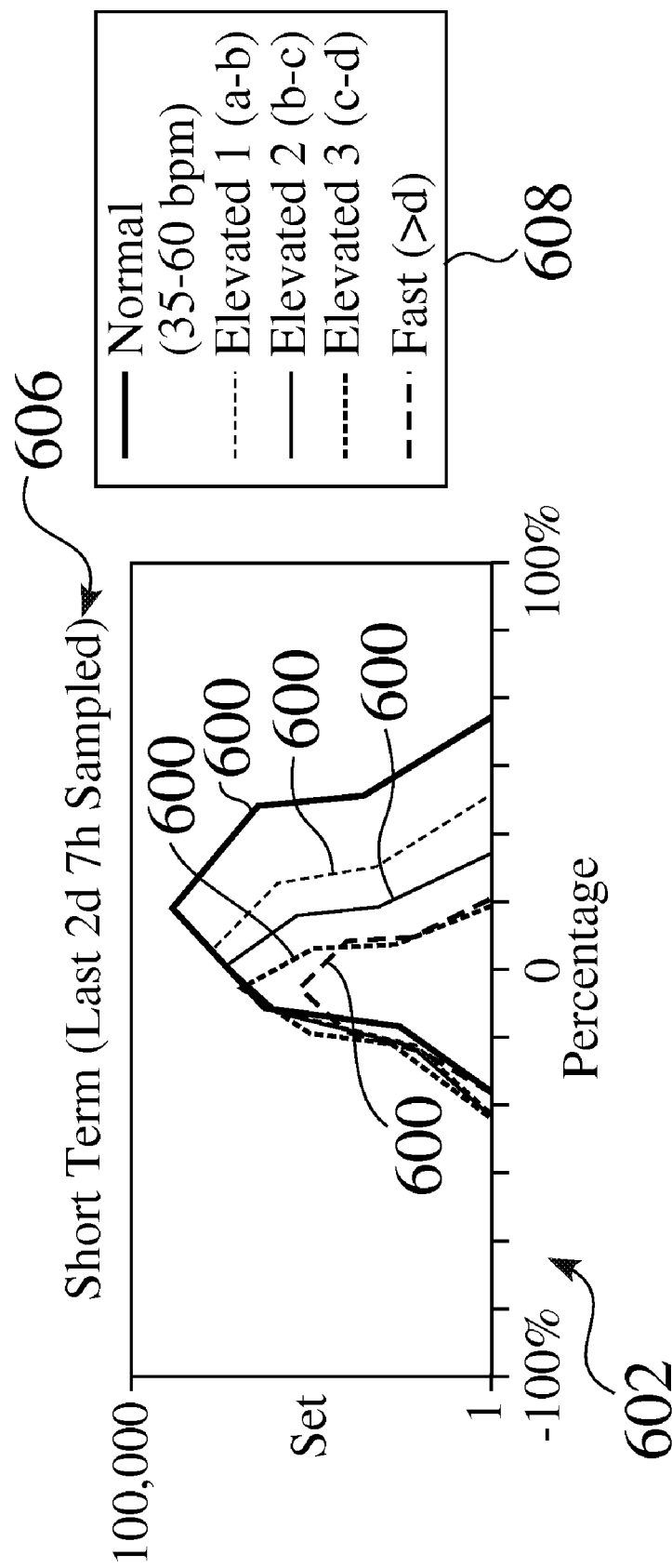

Different types and formats of acquired and processed data may be displayed using the external device 402 or the workstation 414 (both shown in FIG. 4). For example, different histograms may be generated and displayed as shown in FIGS. 6A and 6B. For example, a histogram of five heart rate zones is illustrated by the five different histogram traces 600 on each of the short term graph 602 and long term graph 604. The histogram traces 600 may be color coded based on the heart rate zones (that define heart rate ranges) and that may correlate the histogram traces 600 on each of the short term graph 602 and long term graph 604. The X axis of the short term graph 602 and long term graph 604 represents the STS value, which is a percentage in the exemplary graphs. The X axis optionally can represent, for example, ADC counts or mV. The Y axis represents a value, for example, the number counts per bin or the number of sets. Thus, each of the histogram traces 600, which may generally form a bell curve, graphically illustrate the distribution of STS variations associated with different heart rate ranges.

Data for the short term graph 602 may be stored as the short term histogram data 508 and data for the long term graph 604 may be stored as long term histogram data 510. The short term graph 602 may display the plurality of histogram traces 600 for distributions of variations obtained for a short period of time, for example, for a day or for a week. The histogram traces 600 for distributions of variations obtained for longer periods of time, for example, for a month or for a year, are provided on the long term graph 604, which also may be referred to as a chronic graph. Each of the short term graph 602 and long term graph 604 may include a duration indicator 606 indicating the duration represented by the histogram traces 600. A legend 608 also may be provided to identify the heart rate range corresponding to each of the histogram traces 600. It should be noted that the duration defined by each of the short term graph 602 and long term graph 604 may be modified as desired or needed.

Figure 7:
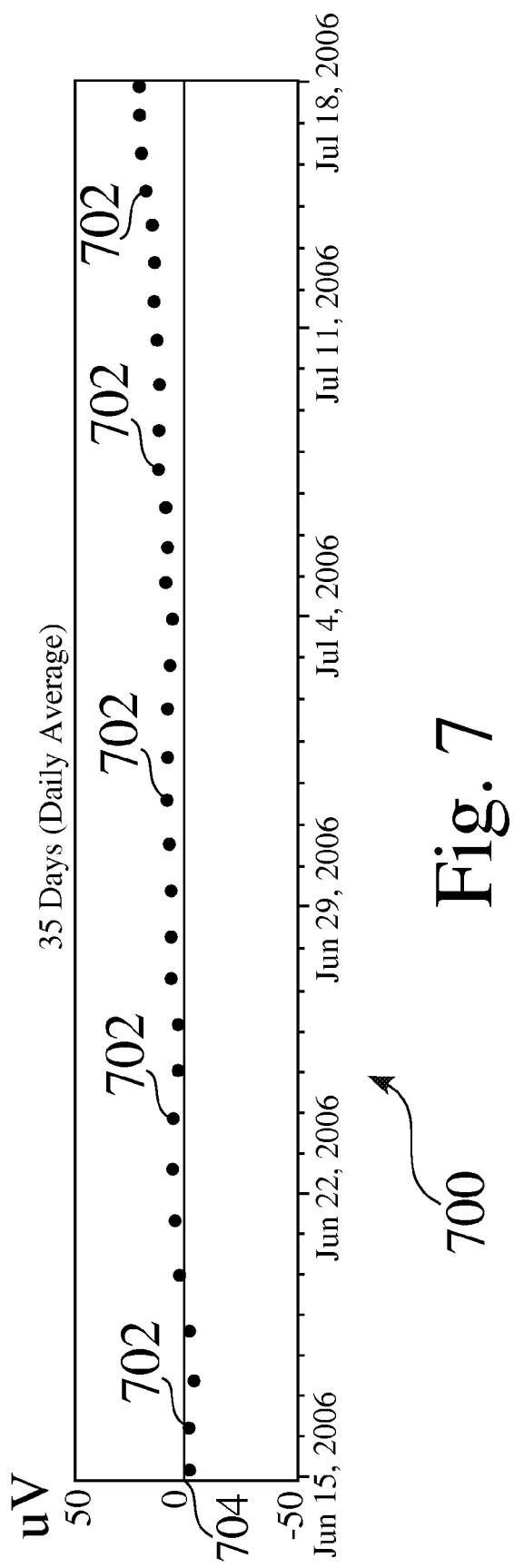
FIG. 7 illustrates a histogram that may be automatically normalized in accordance with an embodiment of the present invention.

Referring again to FIG. 5, the processing unit 502 also includes an STS variance generator module 520 that determines an STS variance. For example, the STS variance generator module 520 acquires STS data from the IEGM data 506 and determines, for example, an STS amplitude difference between a mean STS at a baseline heart rate (that may be determined using the heart rate data 512) compared to the largest amplitude difference at any elevated heart rates. The STS variances over time then may be displayed on a graph 700 as shown in FIG. 7. The X axis of the graph 700 represents time (e.g., days) for the acquired data and the Y axis represents the uV daily average. The Y axis optionally can represent, for example, ADC counts or a percentage value as described herein. The graph 700 includes a plurality of data points 702, for example, one data point 702 for each day that represents a maximum shift between the means of each heart rate bin with zero at a center 704 of the graph 700 and positive data points 702 above the center 704 and negative data points 702 below the center 704.

The processing unit 502 may also include an auto-normalizing histogram generator module 522 that continuously maintains a running average distribution of input values corresponding to the input value assigned to each of a plurality of bins, for example, based on the histogram count data. The number of counts of samples (e.g., identified by the Y axis of graphs 606, 604 or 700) that the STS is shifted up or down by a certain amount (e.g., a predetermined value) corresponding to bins (e.g., identified by the X axis of graphs 606, 604 or 700) are auto-normalized. For example, an auto-normalizing histogram generated by the auto-normalizing histogram generator module 522 includes a histogram with an arbitrary or predetermined number of bins. The histogram continuously maintains a running average distribution of input values corresponding to the input values assigned to each bin, for example, as obtained from the histogram count data 516. The bins are automatically normalized such that the absolute number of the value in each bin is not necessarily a representative value, but the relative distribution between bins is maintained.

Each bin is incremented similar to a normal histogram. It should be noted that a bin is associated with a single value or event, or a range of values or events. Upon the occurrence of an event or sampling a value, the associated bin is incremented, for example, by one. This incrementing count is maintained, for example, as the histogram count data 516. The auto-normalizing histogram generator module 522 automatically divides all bin counts by a predetermined value, for example, two, when any of the bins reaches a predetermined threshold. The predetermined threshold may be a maximum count, which is determined using the histogram count data 516. When dividing any of the bins by the predetermined value, any bin with a non-zero count is rounded up such that the count value is not zero. Each time a count is added (e.g., added to a bin of the histogram), then not only is the histogram count data 516 updated, but a total input counter is also incremented. When the total input counter reaches a maximum value, the total input counter stops counting. Further, each time any bin reaches the maximum count as determined by the predetermined value, then a normalization counter is incremented and the bin counts are each divided by the predetermined value. When the normalization counter reaches a maximum value, the normalization counter stops counting. When either the total input counter or normalization counter reaches the maximum value, a notification is generated indicating that the maximum value has been reached. The total input counter and normalization counter may be used to determine the relative values of bins in each of the different histograms that may have been normalized a different number of times.

In operation, to provide tracking or trending over time, the histograms may be updated continuously and combined on a periodic basis, for example, updated daily. Accordingly, the values in the counters and bins may be reset daily. For example, histogram count data is continuously acquired and updated such that the bin counts corresponding to the acquired data are updated continuously. Thus, data sets defining groups of histograms are acquired and stored. Thereafter, the histograms, for example, the daily histograms optionally may be combined, for example, every week into weekly histograms, and then the weekly histograms combined monthly or bi-monthly into monthly or bi-monthly histograms. For example, each of the corresponding bin counts in each of the histograms from different time periods may be combined (e.g., added together) to generate a combined histogram representing counts over a longer period of time. Accordingly, distributions over days may be combined to form a distribution for a week, distributions for a plurality of weeks may be combined to form a distribution for a month or two months (bi-monthly), etc. These individual or combined histograms can be separately saved.

The processor unit 502 also includes a report generator module 524 that performs report generation, for example, generates the graphs described herein. The reports may be generated for display on a screen or output to hard copy form.

Thus, individual histograms or groups of histograms, for example, based on heart rate ranges are generated and stored. For example, as shown in FIG. 8, a histogram 800 may be generated and used in connection with statistically determining the variability of an STS variation. The histogram 800 is constructed and utilized to analyze, for example, the variability of STS variations 318-320 (shown in FIG. 3) for a particular patient (or a group of patients) caused by non-ischemia related events and ischemia related events. First, STS variations 318-320 are collected over a data collection period (e.g. a day, seven days, a month) for the patient and stored in memory 94 as STS variation data 120 as described above. The histogram 800 plots, on the vertical axis 801, the number of times an STS variation 318-320 occurs, and plots on the horizontal axis 803 the voltage value (or other value of interest) associated with a particular STS variation 318-320. Once the histogram 800 is constructed, certain statistical parameters can be analyzed, such as the average 802 or alternatively the average deviation (not shown), standard deviation (not shown) and the like.

FIG. 9 illustrates a set of histograms 900, 902, 904, 906 and 908 for a particular data collection period where the data has been separated into various heart rate bins or ranges (e.g., <35 bpm, 35-75 bpm, 75-105 bpm, 105-125 bpm, and >125 bpm) from which statistical parameters may be derived. Each histogram 800, 802, 804, 806 and 808 represents a series of STS variations 318-320 that occur for a particular heart rate bin or range during a particular data collection period (e.g., seven days). At least one data collection period may fully or partially occur before the implant of ICD 10 to create a baseline for the patient. The baseline allows a physician to monitor a patient's progress and to determine how well the implant is functioning. The data collection periods can be repeated in a cyclic manner (e.g., 1-7 days after implant, 23-30 days after implant, 53-60 days after implant, 83-90 implant, and the like). Other data collection periods (e.g., one day, three days, five days, ten days, fourteen days, and the like) may be selected. The data collection period may be determined by a user, but the data collection period must be less than 30 days in order not to mask the STS variations, unless auto-normalizing is performed as described herein.

For each data collection period, one or more histograms are created. A histogram is created for a particular range of heart rates. For example, histogram 900 represents STS variations that occur in a patient during a normal heart rate (e.g., 35-60 beats per minute). Histogram 902 represents STS variations that occur in a patient during an elevated heart rate (e.g., 61-80 beats per minute). Histogram 904 represents STS variations that occur in a patient during another elevated heart rate (e.g., 81-100 beats per minute). Histogram 906 represents STS variations that occur in a patient during still another elevated heart rate (e.g., 101-130 beats per minute). Histogram 908 represents STS variations that occur in a patient having a fast heart rate (e.g., greater than 130 beats per minute).

Each histogram 900, 902, 904, 906 and 908 includes a statistical parameter. The statistical parameter may be, for example, an average, an average deviation, or a standard deviation. The user may select the statistical parameter is to be used. For the histograms 900, 902, 904, 906, and 908, a mean value is shown for each histogram: $\mu_{NORM}$ 901, $\mu_{ELEV1}$ 903, $\mu_{ELEV2}$ 905, $\mu_{ELEV3}$ 907, $\mu_{FAST}$ 909. The mean values 901, 903, 905, 907, and 909 are stored in the memory 94 (shown in FIG. 2A) as statistical parameters 121 (shown in FIG. 2B), and the mean values 901, 903, 905, 907 and 909 corresponding to each respective histogram 900, 902, 904, 906, an 908 form a statistical parameter set for a particular data collection period. The statistical parameter set is utilized by the STS trends module 122 (shown in FIG. 2A) to construct an STS trend. Each should be noted that the width of the histograms or bins defining the histograms may be variable, for example, based on the amount of data for a particular variance.

Figure 10:
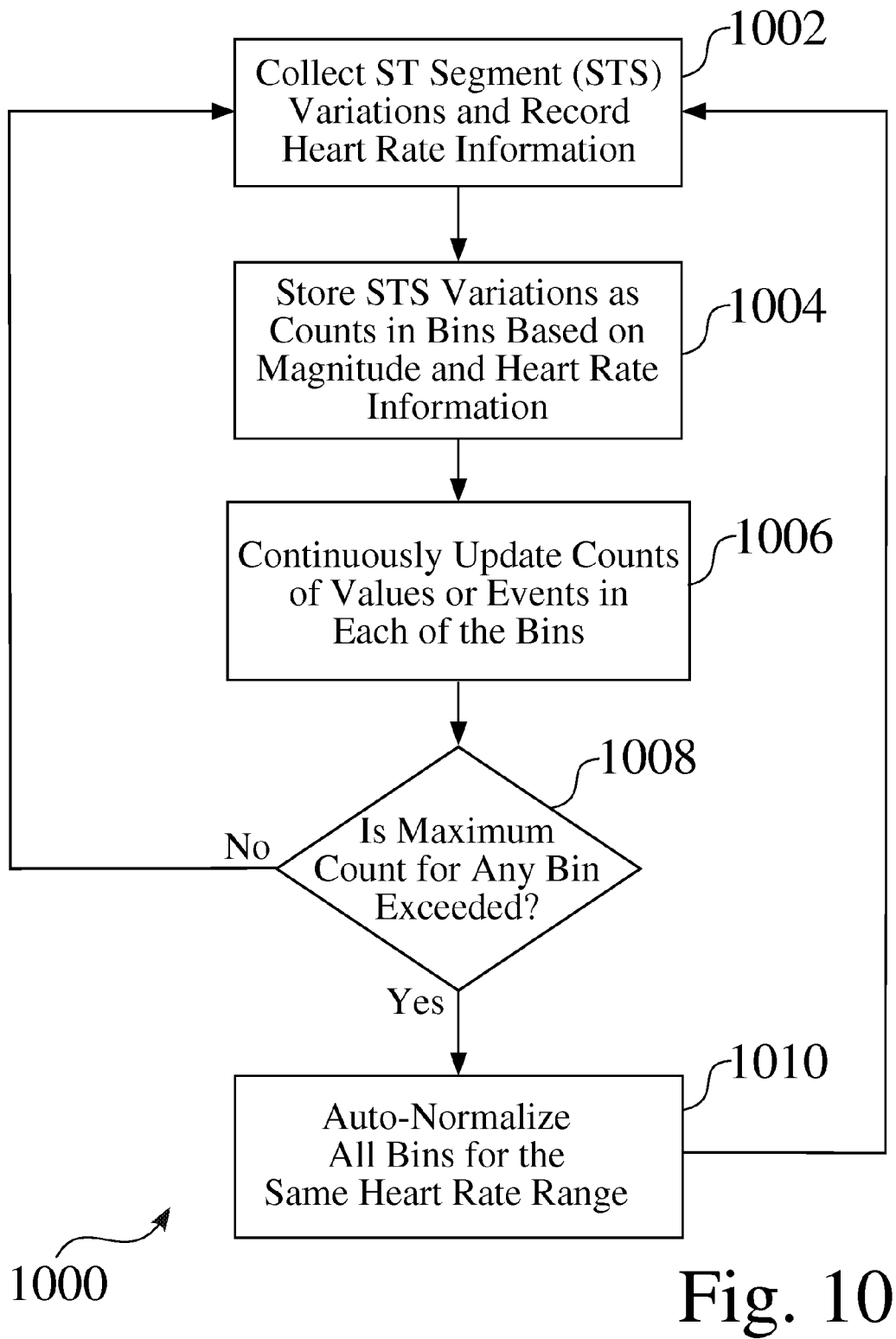
FIG. 10 illustrates a flow diagram for tracking STS variations utilizing normalized histograms in accordance with various embodiments of the present invention.

FIG. 10 illustrates a flow diagram 1000 that depicts a method for tracking STS variations utilizing normalized histograms. The method illustrated by the flow diagram 1000 provides on going data collection and continuous updating of histograms such that STS variations may be used, for example, to determine and update an STS trend in accordance with various embodiments of the present invention. At 1002, the STS variations 318-320 (shown in FIG. 3) are collected on an on going basis. For example, STS variations are acquired on a continuous and real-time basis. Heart rate values are also collected in connection with the STS variations such that the STS variation data includes a corresponding heart rate value. Both the STS variation data and the heart rate values may be stored as STS data 514 and heart rate data 512, respectively, in the memory 94 (shown in FIG. 2A) or the memory 504 (shown in FIG. 5).

Thereafter, at 1004, the collected STS data 514 is stored in a memory of, for example, an implantable medical device and is used to form histograms as described herein. The STS variations are stored as counts in bins based on the magnitude of the variation and the corresponding heart rate value. For example, the STS variation counts are stored in multiple distribution bins for different heart rates. As described above, each STS variation value has a corresponding heart rate value. Each bin may correspond to a user selected or predetermined STS variance or magnitude, or a range thereof (e.g., STS percentage value or mV value), with a separate bin provided for each variance level corresponding to each heart rate range. For example, separate STS variance bins are provided for each of a low heart rate, a normal resting heart rate, a normal active heart rate, an elevated heart rate, a fast heart rate, an arrhythmic heart rate, and a bradycardia heart rate, and the like. For example, the normal heart rate bin (e.g., NORM) for each STS variance level may be defined as a range from 35 to 60 beats per minute, or may be defined as a range from 50 to 80 beats per minute. Furthermore, multiple elevated heart rate conditions may be selected or defined for each STS variance level. For example, one elevated heart rate bin (e.g., ELEV1) for each STS variance may include data relating to heart rates ranging from 60 to 80 beats per minute while another elevated heart rate bin (e.g., ELEV2) for each STS variance may include data relating to heart rates ranging from 81 to 100 heart rates per minute and still another bin (e.g., ELEV3) may include data relating to heart rates ranging from 101 to 130 beats per minute for each STS variance. A fast heart rate bin (e.g., FAST) may include for each STS variance data relating to heart rates in the range of greater than 130 beats per minute.

Thus, the storing includes storing the counts based on respective heart rates and the magnitude of the variation to form groups of histograms. For example, an STS variation of −1.0 mV measured at 86 bpm is placed into the corresponding variance bin (e.g., −1.0 to −2.0 variance bin, −1% to −5% variance bin, etc.) for a normal resting heart rate, while an STS variation of −25 mV measured at 121 bpm is placed in the corresponding variance bin for ELEV3. Once the STS variation values have been stored based on magnitude and heart rate, a histogram for variance bin corresponding to a particular heart rate range may be created. The variance bins may be based on a statistical parameter as determined by the statistical analysis module 103 (shown in FIG. 2A). The statistical parameter may include, for example, an average, an average deviation, a standard deviation, and the like. The statistical analysis module 103 may mathematically determine a statistical parameter, such as the mean, based on the STS variation values stored in STS data 514, for each variance bin corresponding to a particular heart rate. It should be noted that variance bins for each heart rate range may be grouped together.

For each of the bins corresponding to the different heart rates, the count of the number of recorded values or events is continuously updated at 1006 (e.g., histogram updated). For example, for each variance or magnitude bin corresponding to each heart rate a total number of counts is continuously updated based on the on going data collection. The counts may be stored as histogram count data 516 in the memory 504 (both shown in FIG. 5). Each time a count is added to any of the bins, the total input counter is incremented.

Thereafter, at 1008 a determination is made as to whether a maximum count value (e.g., a predetermined maximum value) is exceeded for any single variance bin corresponding to a particular heart rate range. If the maximum count has been exceeded, then at 1010 all variance bins corresponding to the same heart rate range for the exceeded variance bin are auto-normalized as described herein. For example, each of the variance bins corresponding to the same heart rate range is divided by a predetermined value (e.g., two or three). The normalization counter is also incremented each time auto-normalizing is performed. Thereafter, STS variations and corresponding heart rate information continue to be collected at 1002. Also, if the maximum count value is not exceeded as determined at 1008, then STS variations and corresponding heart rate information continue to be collected at 1002.

It should be noted that STS trend analysis module 105 (shown in FIG. 2A) may construct STS trends 122 (shown in FIG. 2B) based on the collected data. These STS trends may be provided to a user, for example, as a display, a pictorial representation, a symbolic representation, a graph, a bar graph, a chart, a histogram (as described herein an illustrated in FIGS. 6 through 9), a pie chart, a Venn diagram, and combinations thereof as described in more detail above. The STS trend 122 may indicate an abnormal physiology, such as an ischemia, a myocardial infarction, a post-myocardial infarction, a silent myocardial infarct, an arrhythmia, a fibrillation, a heart block or a congestive heart failure.

It should also be noted that the count data in each of the total input counter and the normalization counter may be used to determine the relative counts of the bins in each of the different histograms that may have been normalized a different number of times. For example, using the normalization counter, the relative value between different histograms may be restored by accounting for the differences in the number of times the different histograms were normalized. Further, using the total input counter, the total values of the bins from the different normalized histograms may be determined.

Figure 11:
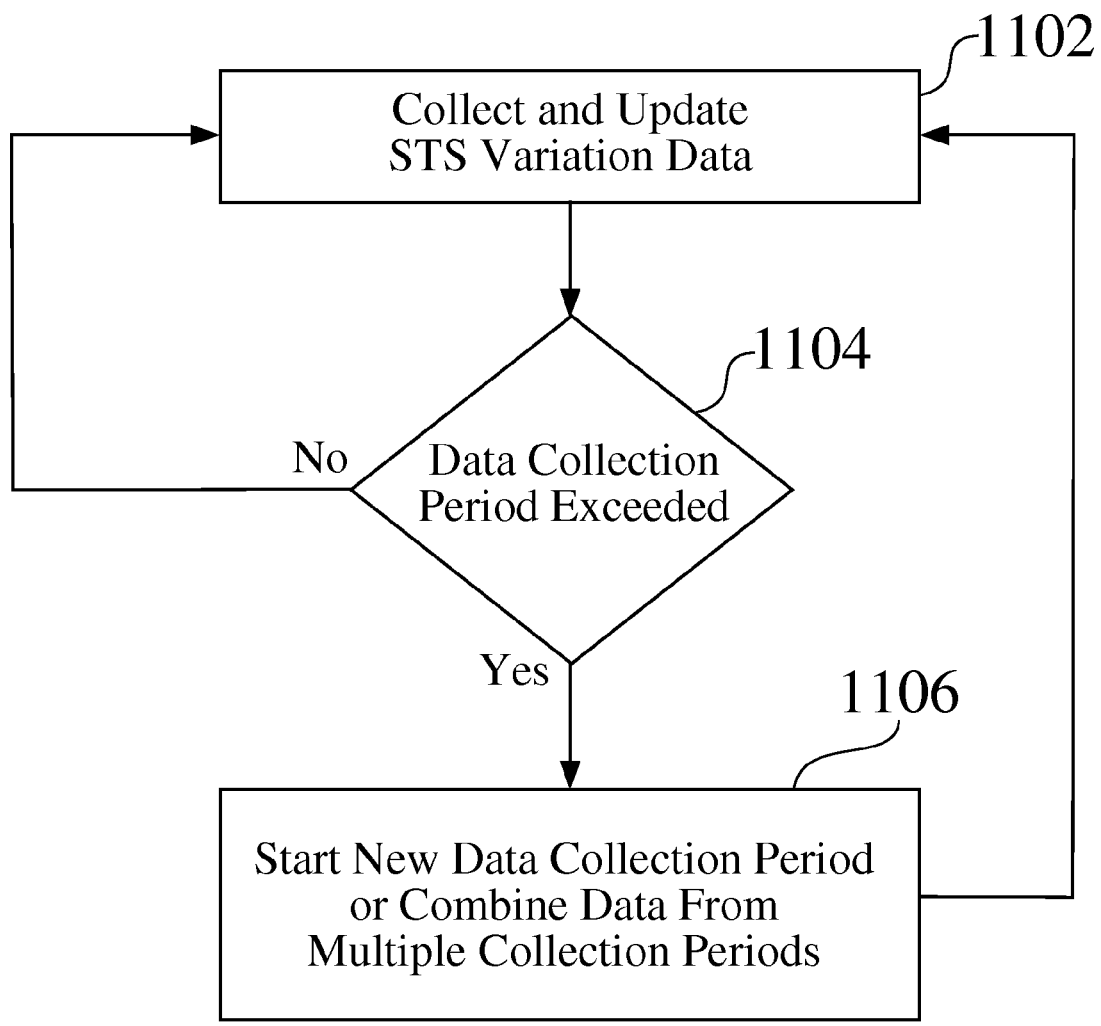
FIG. 11 illustrates a flow diagram for combining collected STS variation data stored as normalized histograms in accordance with various embodiments of the present invention.

FIG. 11 illustrates a flow diagram 1100 that depicts a method for optionally combining collected STS variations stored as normalized histograms. Specifically, at 1102 STS variation data is collected and updated, for example, using the method illustrated by the flow diagram 1000 (shown in FIG. 10). Thereafter, a determination is made at 1104 as to whether a predetermined or user defined data collection period has been exceeded. For example, a determination is made as to whether data, such as STS variation data, has been collected for more than a day, a week, two weeks, a month, two months, etc. If the data collection period has not been exceeded, then STS variation data continues to be collected and updated at 1102.

If the data collection period has been exceeded, then at 1106 a new data collection period is started and/or data from multiple collection periods are combined as described herein. For example, if data has been collected for one day, then a new data collection period is started with each of the variance bins reset. Additionally, and for example, if data for seven days has been collected, the data is then combined to define a weekly data set. It should be noted that as data is collected or combined, auto-normalizing may continue to be performed. Thereafter, STS variation data continues to be collected and updated at 1102.

Thus, in accordance with certain embodiments, methods and systems are provided that are able to measure STS variations over time that are stored in an implantable medical device for later access. For example, STS histograms may be generated and later accessed such that an implantable medical device may track STS variations using the histograms. The STS histograms also may be auto-normalized.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the specific components and processes described herein are intended to define the parameters of the various embodiments of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

What is claimed is:

1. An implantable medical device, comprising:
   an input configured to receive cardiac signals, each cardiac signal having an associated heart rate and including a segment of interest;
   a processor configured to determine segment variations of the segment of interest in the cardiac signals, the processor determining a heart rate associated with each of the segment variations, each heart rate falling within a corresponding heart rate range; and
   a memory configured to store a group of histograms for a corresponding group of heart rate ranges, the histograms storing distributions for the segment variations within corresponding heart rate ranges, wherein at least one of the histograms includes a series of bins corresponding to different segment variations, the bins being automatically normalized by the processor when a count in at least one of the bins reaches a predetermined threshold.

2. The device of claim 1, wherein the segment of interest represents an ST segment.

3. The device of claim 1, wherein the processor is configured to identify at least one of a segment shift and a segment deviation as the segment variation.

4. The device of claim 1, wherein the processor is configured to identify the segment variation with respect to a reference level, the reference level presenting one of i) a baseline value for the segment of interest and ii) a value for a reference segment with the cardiac signal.

5. The device of claim 1, wherein first and second groups of histograms store distributions of the segment variations over different first and second periods of time.

6. The device of claim 1, wherein the processor maintains running average distributions for the segment variations input to each of the histograms and auto-normalizes the histograms based on the running average distributions.

7. The device of claim 1, further comprising at least one total input counter associated with the histograms, the total input counter maintaining a count of a total number of segment variations stored in a corresponding histogram.

8. The device of claim 1, further comprising at least one total input counter associated with the histograms, the total input counter maintaining a count of a total number of segment variations stored in a corresponding histogram, the processor utilizing the count in the total input counter to determine relative values of bins in the histograms.

9. The device of claim 1, further comprising at least one normalization counter associated with the histograms, the normalization counter maintaining a count of a number of times a corresponding histogram is normalized.

10. The device of claim 1, wherein the processor is configured to divide the count within each bin in the series of bins for at least one of the histograms by a normalizing value to reduce counts within each bin in the series of bins and maintain a relative distribution for the histogram.

11. The device of claim 1, wherein each of the bins corresponds to one of a different percentage value range or a magnitude value range.

12. The device of claim 1, wherein the cardiac signals are obtained on one of a heart beat by heat beat basis and a set by set basis.

13. The device of claim 1, wherein a plurality of groups of histograms correspond to distributions of the segment variations over a plurality of time periods and wherein the processor is configured to combine the plurality of groups of histograms into a single histogram.

14. The device of claim 1, wherein the group of histograms includes histograms rotated on a daily basis.

15. A method for maintaining myocardial data in an implantable medical device, comprising:
   receiving myocardial data including segments of interest;
   associating the segments of interest with heart rate ranges;
   generating a group of histograms corresponding to each of the heart rate ranges, the group of histograms including distributions for segment variations for the segments of interest, wherein the histograms each include a series of bins corresponding to different segment variations;
   storing the group of histograms in the implantable medical device; and
   automatically normalizing the bins in at least one of the histograms when a count in at least one of the bins reaches a predetermined threshold.

16. The method of claim 15, further comprising generating histograms based on a predetermined time period.

17. The method of claim 15, further comprising automatically normalizing bins in at least one of the histograms upon determining that a bin corresponding to a particular segment variation has reached a maximum count.

18. The method of claim 15, wherein the distributions include running averages.

19. The method of claim 15, wherein the histograms comprise ST shift histograms.

20. A non-transitory computer readable medium for use in an implantable medical device having a memory and a programmable controller, the computer readable medium having instructions to direct the programmable controller to:
   i) receive myocardial data including segments of interest;
   ii) associate the segments of interest with heart rate ranges; and
   iii) generate a group of histograms corresponding to each of the heart rate ranges, the group of histograms including distributions for segment variations for the segments of interest, wherein the histograms each include a series of bins corresponding to different segment variations;
   iv) automatically normalize the bins in at least one of the histograms when a count in at least one of the bins reaches a predetermined threshold; and
   direct the memory to:
   i) store the group of histograms in the implantable medical device.

* * * * *